‎

US008367887B2

(12) United States Patent
Hayashi et al.

(10) Patent No.: US 8,367,887 B2
(45) Date of Patent: Feb. 5, 2013

(54) NORMAL-TENSION GLAUCOMA MODEL AND METHOD FOR EVALUATION OF TEST SUBSTANCES BY USING SAME

(75) Inventors: Takuma Hayashi, Matsumoto (JP); Yasuko Takahashi, Matsumoto (JP); Tomoko Yanagidaira, Matsumoto (JP); Shunichiro Taniguchi, Matsumoto (JP); Toshinori Murata, Matsumoto (JP)

(73) Assignee: Shinshu University, Matsumoto-Shi (JP)

( * ) Notice: Subject to any disclaimer, the term of this patent is extended or adjusted under 35 U.S.C. 154(b) by 13 days.

(21) Appl. No.: 12/668,838

(22) PCT Filed: Jul. 11, 2008

(86) PCT No.: PCT/JP2008/062616
§ 371 (c)(1),
(2), (4) Date: Mar. 25, 2010

(87) PCT Pub. No.: WO2009/008511
PCT Pub. Date: Jan. 15, 2009

(65) Prior Publication Data
US 2010/0204311 A1 Aug. 12, 2010

(30) Foreign Application Priority Data

Jul. 12, 2007 (JP) ................ 2007-183306

(51) Int. Cl.
*G01N 33/00* (2006.01)
*A01K 67/027* (2006.01)
*A01K 67/033* (2006.01)

(52) U.S. Cl. ............... 800/3; 800/8; 800/13; 800/14; 800/18

(58) Field of Classification Search ............ 800/3, 8, 800/13, 14, 18
See application file for complete search history.

(56) References Cited

U.S. PATENT DOCUMENTS

| 2003/0027745 | A1* | 2/2003 | Repine .................. 514/1 |
| 2005/0277698 | A1 | 12/2005 | Hughes et al. |
| 2007/0011758 | A1 | 1/2007 | Tanaka et al. |

FOREIGN PATENT DOCUMENTS

| EP | 1 619 248 A1 | 1/2006 |
| JP | A-2004-313188 | 11/2004 |
| WO | WO 2004/092371 A1 | 10/2004 |

OTHER PUBLICATIONS

Denning and Priddle. Reproduction 126:1-11, 2003.*
Lu, Z.Y. et al., "Age-Related Neural Degeneration in Nuclear-Factor κB P50 Knockout Mice," *Neuroscience*, 2006, pp. 965-978, vol. 139, No. 3.
Anonymous, "Strain Name: B6.Cg-*Nfkb1*$^{tm1Bal}$/J," *The Jackson Laboratory*, 2006, pp. 1-18, retrieved from http://jaxmice.jax.org/strain/006097.html.
Yu, ZaiFang et al., "Lack of the p50 Subunit of Nuclear Factor-κB Increases the Vulnerability of Hippocampal Neurons to Excitotoxic Injury," *The Journal of Neuroscience*, Oct. 15, 1999, pp. 8856-8865, vol. 19, No. 20.
Choi, Jun-Sub et al., "Failure to Activate NF-κB Promotes Apoptosis of Retinal Ganglion Cells Following Optic Nerve Transection," *Brain Research*, 2000, pp. 60-68, vol. 883, No. 1.
European Search Report issued in European Application No. 08791097.2 dated Jun. 21, 2010.
Takahashi et al.; "Development of spontaneous optic neuropathy in NF-κBp50-deficient mice: requirement for NF-κBp50 in ganglion cell survival;" *Neuropathology and Applied Neurobiology*; 2007; pp. 692-705; vol. 33; No. 6.
Miller et al.; "Lactate Treatment Causes NF-κB Activation and CD44 Shedding in Cultured Trabecular Meshwork Cells;" *Investigative Ophthalmology & Visual Science*; 2007; pp. 1615-1621; vol. 48; No. 4.
Wang et al.; "Ultrasound Activates the TM ELAM-I/IL-I/NF-κB Response: A Potential Mechanism for Intraocular Pressure Reduction after Phacoemulsification;" *Investigative Ophthalmology & Visual Science*; 2003; pp. 1977-1981; vol. 44; No. 5.
Krishnamoorthy et al.; "Photo-oxidative Stress Down-modulates the Activity of Nuclear Factor-κB via Involvement of Caspase-1, Leading to Apoptosis of Photoreceptor Cells;" *The Journal of Biological Chemistry*; 1999; pp. 3734-3743; vol. 274; No. 6.
Korhonen et al.; "Age-related changes in the regulation of transcription factor NF-κB rat brain;" *Neuroscience Letters*; 1997; pp. 61-64; vol. 225; No. 1.
International Search Report for International Application No. PCT/JP2008/062616, issued Aug. 19, 2008.

* cited by examiner

*Primary Examiner* — Marcia S Noble
(74) *Attorney, Agent, or Firm* — Oliff & Berridge, PLC (57) ABSTRACT

It is intended to provide a simple normal-tension glaucoma model capable of spontaneously, age-dependently and surly developing conditions similar to symptoms of normal-tension glaucoma which occurs more frequently in elder people, and a method of evaluating therapeutic effect on normal-tension glaucoma whereby a drug useful in treating and diagnosing can be conveniently screened by using the normal-tension glaucoma model. A normal-tension glaucoma model comprising a nonhuman mammal, which is deficient in a transcriptional regulator NF-κBp50 and thus spontaneously develops the normal-tension glaucoma symptom age-relatedly, an organ or a tissue thereof or cells collected from any of the same. A method of evaluating therapeutic effect on normal-tension glaucoma of a test substance which comprises administering or adding the test substance to the above-described nonhuman mammal, an organ or a tissue thereof or cells collected from any of the same, and measuring a morphological defect, cell count, pressure, the expression amount or activity strength of a protein, the expression amount of a nucleic acid and/or the activity strength of an antibody in the organ, tissue and/or cells as indication(s) for the evaluation.

4 Claims, 6 Drawing Sheets
(2 of 6 Drawing Sheet(s) Filed in Color)

NORMAL-TENSION GLAUCOMA MODEL AND METHOD FOR EVALUATION OF TEST SUBSTANCES BY USING SAME

TECHNICAL FIELD

The present invention relates to a normal-tension glaucoma model capable of age-dependently developing conditions similar to symptoms of normal-tension glaucoma which occurs more frequently in middle-aged and elder people, and a method for evaluation of therapeutic effect on normal-tension glaucoma using the normal-tension glaucoma model. The present invention also relates to a therapeutic agent for normal-tension glaucoma, and a diagnosis and a risk prediction of normal-tension glaucoma.

BACKGROUND OF THE INVENTION

Glaucoma, one of the leading causes of blindness, is a disease characterized by decrease in visual field resulted from injury to optic nerves caused by aging or negative lifestyle habits, for example stressful environment.

Elevated intraocular pressure has been regarded as a major risk factor for developing glaucoma. Light entered through the crystalline lens of an eye is captured by the light receptors in retina, and biosignals given off by such phenomenon are transmitted to optic nerves in the retina. Then, the biosignals are transmitted to the brain through the optic nerve head located at the back of the eye, where the optic nerves are bundled. Development of high-tension glaucoma due to elevated intraocular pressure involves several stages. The first stage involves gradual injury to the optic nerves in the retina caused by atrophia and enlargement thereof, followed by the next stage which involves apoptosis of the retinal ganglion cells (RGCs), a type of neuron located in the retina. Then, it leads excavation of the optic nerve head that causes gradual decrease in visual field which eventually causes blindness. Several lines of evidence have been gradually accumulating from recent studies of high-tension glaucoma that suggest several risk factors such as ischemia, high glutamate intake and genetic background which play important roles in the pathogenesis and development of glaucoma. Furthermore, autoimmunity that directly recognizes retinal proteins has been associated with developing glaucoma.

Although the risk factor remains unknown, glaucoma occurs even at normal intraocular pressure with high frequency. In normal-tension glaucoma, clinical findings of (1) intraocular pressure within the range of normal level (10 to 21 mmHg), (2) constriction and excavation of optic nerve head periphery, (3) loss of a retinal nerve fiber layer, (4) metamorphosis and backward deviation of the optic nerve at lamina cribrosa (lamina orbital's) and (5) decrease in retinal ganglion cells and glial cells can be clinically and comprehensively observed, and normal-tension glaucoma is characterized by the specific lesions of the optic nerves.

Similar to high-tension glaucoma, normal-tension glaucoma also involves stages of atrophia and enlargement of the retinal ganglion cells, apoptosis of the retinal ganglion cells and excavation of the optic nerve head that causes gradual decrease in visual field which eventually causes blindness. The morbidity of normal-tension glaucoma patients in Japan is high. In fact, the morbidity thereof in the total population is said to be several percentage. In particular, 1 in 28 people (3.6%) aged 40 or over is a normal-tension glaucoma patients. Moreover, in elder patients aged 40 or over, mail or female, the morbidity of normal-tension glaucoma significantly increases with age. Although the morbidity of normal-tension glaucoma in people under the age of 40 is only approximately 0.1%, the morbidity increases to slightly fewer than 2% in 40s, slightly more than 2% in 50s, about 6% in 60s and about 7% in 70s or older. Normal-tension glaucoma is the second leading cause of blindness in Japan after diabetic retinopathy, but the pathogenesis and pathogenic mechanism thereof remain unknown. Therefore, there is no fundamental treatment for narrowed visual field caused by the development of normal-tension glaucoma. Consequently, allopathy using ophthalmic drug such as a sympatholytic drug, a sympathomimetic drug, a parasympathomimetic drug, a prostaglandin-related drug and a carbonic anhydrase inhibitor is performed to decrease the intraocular pressure.

To study pathogenic mechanism of normal-tension glaucoma or to develop therapeutics, a therapeutic agent, a preventive method or a preventive agent thereof, a normal-tension glaucoma model capable of developing conditions similar to distinctive chronic conditions of human normal-tension glaucoma which age-dependently occur more frequently and further develop in people at the age of 40 or older is desired.

In Japanese unexamined patent publication No. 2004-313188, an animal model of normal-tension glaucoma prepared by administering an aluminum compound thereto to induce injury to optic nerve axons is disclosed. However, according to this animal model, the injury is forcibly induced by the external drug administration, and thus the animal model is not capable of spontaneously developing the injury. Moreover, the animal model does not develop the injury age-dependently.

SUMMARY OF THE INVENTION

The present invention has been developed to solve the foregoing problems. It is an object of the present invention to provide a simple normal-tension glaucoma model capable of spontaneously, age-dependently and surely developing conditions similar to symptoms or clinical findings of normal-tension glaucoma which occurs more frequently in middle-aged and elder people, and a method for evaluation of therapeutic effect on normal-tension glaucoma whereby a drug useful in treating and diagnosing can be conveniently screened by using the normal-tension glaucoma model. It is another object of the present invention to provide a safe and convenient therapeutic agent for normal-tension glaucoma, and a simple and secure method for a diagnosis and a risk prediction of normal-tension glaucoma.

The normal-tension glaucoma model of the present invention developed to accomplish the above-mentioned objects comprises;
  a nonhuman mammal that is deficient in transcription factor NF-κBp50 and thereby spontaneously and age-dependently develops symptoms of normal-tension glaucoma,
  an organ or tissue thereof, or
  cells harvested from one of them.

In the normal-tension glaucoma model, the nonhuman mammal is preferably a mouse.

The method for evaluation of therapeutic effect of test substances on normal-tension glaucoma of the present invention comprises;
  administering or adding of the test substances to the nonhuman mammal that is deficient in transcription factor NF-κBp50 and thereby spontaneously and age-dependently develops symptoms of normal-tension glaucoma, the organ or tissue thereof, or the cells harvested from one of them, and measuring of an index for the evaluation selected from a morphological change, a cell count, pressure, expression amount or activity of protein, expression amount of nucleic acid and/or activity of an antibody in the organ, the tissue and/or the cells.

The method for evaluation comprises;
a pre-step of respectively keeping the nonhuman mammal under conditions with and without administration of the test substances, or of respectively culturing the cells under conditions with and without addition of the test substances,
a step of measuring the index by observing, determining or detecting thereof, and
a post-step of comparing the index under the condition with administration of the test substances to the index under the condition without administration of the test substances, or of comparing the index under the condition with addition of the test substances to the index under the condition without addition of the test substances, and then performing the evaluation of the test substances followed by screening thereof.

In the method for evaluation, the nonhuman mammal is preferably a mouse.

In the method for evaluation, the organ or the tissue is selected from the group consisting of an eye, a retina, an optic nerve, retinal ganglion cells, a retinal ganglion cell layer, a retinal nerve fiber layer, a retinal granular layer, a retinal plexiform layer, an optic nerve axon or an optic nerve head.

In the method for evaluation, further N-methyl D aspartate (NMDA) or salt thereof is administered or added other than the test substances.

In the method for evaluation, the test substances are at least one selected from the group consisting of a NMDA receptor antagonist, a calcium inhibitor, an I-κB degradation inhibitor, a NF-κB decoy oligo nucleic acid and a calcineurin inhibitor.

The method for evaluation of therapeutic effect of test substances on normal-tension glaucoma of another present invention comprises;
administering or adding of the test substances to an individual of a nonhuman mammal or cells of the nonhuman mammal or a human and
measuring of an index for the evaluation selected from expression amount or activity of transcription factor NF-κBp50 in the individual or the cells.

The method for evaluation comprises;
a pre-step of respectively culturing the cells in a culture solution under conditions with and without addition of the test substances,
a step of measuring the index of the expression amount and the activity of the transcription factor NF-κBp50 in the culture solution or in the cells therein, and
a post-step of the index under the condition with addition of the test substances to the index under the condition without addition of the test substances, and then performing the evaluation of increase in the expression amount or improving of the activity under the conditions with addition of the test substances followed by screening of the test substances.

In the method for evaluation, the cells are derived from and isolated from the nonhuman mammal that is deficient in the transcription factor NF-κBp50 and thereby spontaneously and age-dependently develops symptoms of the normal-tension glaucoma or from the human of glaucoma patient, or are a cell strain thereof.

The method for evaluation comprises;
a pre-step of respectively keeping the nonhuman mammal under conditions with and without administration of the test substances,
a step of measuring the index of the expression amount and the activity of the transcription factor NF-κBp50 in blood or the cells of the nonhuman mammal, and
a post-step of comparing the index under the condition with administration of the test substances to the index under the condition without administration of the test substances, and then performing the evaluation of increase in the expression amount or improvement in the activity under the conditions with administration of the test substances followed by screening of the test substances.

In the method for evaluation, the nonhuman mammal is preferably a mouse.

The therapeutic agent for normal-tension glaucoma of another present invention comprises an inhibitor for activity of transcriptional inducer of transcription factor NF-κBp50. Inhibition of the transcriptional activity of transcription factor NF-κBp50 is useful in treatment of normal-tension glaucoma.

In the therapeutic agent for normal-tension glaucoma, the inhibitor is at least one selected from the group consisting of NMDA receptor antagonist, a calcium inhibitor, an I-κinhibitor, a NF-κB decoy oligo nucleic acid and a calcineurin inhibitor.

The therapeutic agent for normal-tension glaucoma of another present invention comprises an accelerator for expression of transcription factor NF-κBp50. Acceleration of the expression of transcription factor NF-κBp50 is useful in treatment of normal-tension glaucoma.

In the therapeutic agent for normal-tension glaucoma, the accelerator is a transfection agent, which transfects a gene for code of NF-κBp50. Transfecting the gene for code of NF-κBp50 by such transfection agent is used in treatment of normal-tension glaucoma.

The method for a diagnosis of normal-tension glaucoma of another present invention comprises;
measuring of expression amount or activity of NF-κBp50 included in one selected from the group consisting of an organ and tissue derived from human of examinee, harvested cells from them, and collected blood from the human.

The method for a risk prediction of normal-tension glaucoma of another present invention comprises;
measuring of existence of a gene arrangement for code of NF-κBp50 in one selected from the group consisting of an organ and tissue derived from human of examinee, harvested cells from them, and collected blood from the human.

The normal-tension glaucoma model of the present invention is capable of spontaneously, age-dependently and surly developing conditions similar to distinctive chronic symptoms or clinical findings of human normal-tension glaucoma which occurs more frequently in middle-aged and elder people.

This model is capable of developing conditions similar to symptoms in patients with normal-tension glaucoma by pathogenic mechanism resembling that of human normal-tension glaucoma wherein the lack of transcription factor NF-κBp50 induces the apoptosis of the optic nerves age-dependently, which causes an excavation of the optic nerve head, and also autoimmunity that directly recognizes proteins expressed in retinal ganglion cells (RGCs) is produced. Therefore, this model is useful for investigating pathogenic mechanism of normal-tension glaucoma by investigating the relationship between activation of the transcription factor and development, atrophia or apoptosis of the optic nerves as well as investigating mechanism of atrophia and enlargement of the optic nerves.

According to the method for evaluation using the normal-tension glaucoma model, a drug useful in treating and diagnosing can be simply and surely screened. Furthermore, this method for evaluation is useful not only for investigating the pathogenic mechanism of human normal-tension glaucoma but also developing a method for treating and preventing, a drug used for such treatment and prevention, and an evaluation of therapeutic effect using the same.

The therapeutic agent for normal-tension glaucoma of the present invention is safe and surly medicinal, and it is useful for simple treatment.

Furthermore, the methods for the diagnosis and the risk prediction of normal-tension glaucoma of the present invention are useful for early detection and early treatment. Also, by using the before-mentioned therapeutic agent for normal-tension glaucoma, it is capable of treating normal-tension glaucoma.

BRIEF EXPLANATION OF THE DRAWINGS

This application contains at least one photograph executed in color.

DETAILED EXPLANATION OF THE INVENTION

Hereunder, preferred embodiments of the present invention are explained in detail. However, the scope of the present invention is not intended to be limited to these embodiments.

The normal-tension glaucoma model of the present invention is made up of a transcription factor NF-κBp50-deficient mouse.

The transcription factor NF-κBp50 has been known to play a key role in biological defense mechanism, growth in neuronal cells and memory. In addition to these, according to the normal-tension glaucoma model, the transcription factor NF-κBp50 is also important not only in increase in retinal ganglion cells and electron transfer system, but also pathogenesis and development of glaucoma due to decrease in the transcription factor activation which occurs with age.

p50 (NFKB1) is bound to p65 (RelA) to form the NF-κB complex. The p50 (NFKB1)/p65 (RelA) heterodimer is the most abundant form of NF-κB among NF-κB family constituted with sub-type thereof. The NF-κB complex is inhibited by I-κB proteins, which inactivate NF-κB by trapping it in the cytoplasm. Extracellular stimulus leads phosphorylation of serine residues on I-κB proteins by kinases (IKKβ or IKKγ). Via the ubiquitination pathway, I-κB of the phosphorylated form is destructed by proteasome and then NF-κB becomes free form allowing the activation thereof. Activated NF-κB translocates into the nucleus and binds DNA at specific DNA sequence (NF-κB binding motifs), and then markedly activates gene transcription. On the other hand, p50 is required for binding DNA, and p65 is an essential factor for gene transcriptional activation.

The wide functional implications of NF-κB are reflected in the reviews of the relationship to cancer, on the relationship to neuronal plasticity and the treatment of neurologic disorders. In the central nervous system, NF-κB is expressed ubiquitously in both neuronal and glial cells where it plays a key role in various physiological mechanisms such as synaptic activity, learning, memory, survival and apoptosis.

NF-κB mediates pathophysiological events associated with acute neurodegeneration including trauma, seizure and ischemica and also chronic neurodegeneration such as Alzheimer disease. On the other hand, NF-κB prevents apoptosis within hepatic cells and the like, although it also appears to promote NMDA-induced apoptosis in neurons.

To clarify the precise roles of NE-KB in neuronal cell death, the phenotypes of NF-κBp50-deficient mice was analyzed, and the involvement of NF-κBp50 in retinal ganglion cell death was revealed.

Age-related survival of the retinal ganglion cells was investigated by the method for evaluation of therapeutic effect on normal-tension glaucoma using the normal-tension glaucoma model comprising NF-κBp50-deficient mice. It was found that these mice exhibited many features resembling human glaucoma disease.

Hereunder, examples in which therapeutic effect on normal-tension glaucoma was evaluated using a normal-tension glaucoma model of the present invention are explained in detail.

The reagents, animals and the method for evaluation used for examples are as follows.

(Examined Animals)

All wild-type (normal-type), heterozygous (NF-κBp50-deficience in one allele on a chromosome) and homozygous (NF-κ50-deficience in both alleles on a chromosome) mice examined in the embodiments were littermates of NF-κBp50-deficient F8 mice generated by backcrossing with C57BL/6J mice. Mice homozygous for the Nfkb$^{1tm1Bal}$ target mutation, which have approximate B6/129-F2 genetic backgrounds, were purchased from Jackson Laboratories (ME, USA), and C57BL/6 mice were also purchased from CLEA Japan Inc. (Tokyo, Japan). These mice were kept in a specific pathogenfree (SPF) room at Shinshu University animal facilities in accordance with local guidelines of Shinshu University.

(Preparation of NF-κBp50-Deficient Mice)

By using a targeting vector, a gene region including initiating-methionine for NF-κBp50 was replaced to a drug-resistant gene (i.e. a neomycin-resistant gene) through homologous recombination to avoid production of NF-κBp50 from the gene. Concretely, the targeting vector was transfected into mouse embryonic stem (ES) cells having totipotency, which are ES cells of 129 mouse strain (i.e. E14 cells) and are at 4 millions cell/ml, by an electroporation technique under condition of 250 V, 250 micro F, 40-50 m sec. of time-constant at room temperature. And homologous-recombined cells were selected with referring neomycin-resistance as an index by using 150 mg/ml of neomycin analogue: G418. It was verified by Southern blotting technique that the DNA gene region of NF-κBp50 was replaced to the drug-resistant gene through the homologous recombination in the cells selected by G418 in actual fact. And by reverse transcriptase polymerase chain reaction (RT-PCR) technique and Western blotting technique, further it was verified that NF-κBp50 and mRNA of NF-κBp50 were not expressed. ES cells (i.e. recombined ES cells), which are deficient in one of NF-κBp50 gene among homologous chromosomes by above-mentioned general homologous recombination, are obtained. And then chimeric mice were derived from the recombined ES cells (see; Sha, W. et al., Cell, 80, 321-330, 1995), as follows. The recombined ES cells were injected to normal mouse embryos in blastocyst-stage or 8 cell-stage by a microinjection technique or an agglutination technique. Thus obtained chimeric cells were transplanted to a uterine horn of female mice under pseudopregnancy. The transplanted mice were kept under normal conditions to generate neonatal chimeric mice. It is preferable that the recombined ES cells be injected to embryos of C57BL/6 strain mice. The chimeric mice have normal cells and cells derived form the recombined ES cells as somatic cells and germ cells. The chimeric mice were crossed with wild-type mice, preferably C57BL/6 strain mice such as C57BL/6J strain mice to generate neonatal heterozygous mice-F1. Specifically the male chimeric mice were crossed with the female wild-type mice to generate the heterozygous mice-F1. When the germ cells of the chimeric mice for crossing were derived from above-mentioned recombined ES cells, namely the ES cells which were deficient in one of inherent NF-κBp50 gene among homologous chromosomes, the desired heterozygous mice-F1 which were deficient in functions of the gene were given. By analysis of DNA extracted from tails of mice-F1 using Southern blotting technique or PCR technique, it was verified that the desired gene-type were induced therein.

It is preferable that genetic backgrounds of the NF-κBp50-deficient mice be isogenic with one of the C57BL/6 strain mice possibly for the present invention. Hence it is necessary that procedures of crossing between the above-mentioned given heterozygous mice-F1 and C57BL-6 strain mice such as C57BL-6J strain mice, and furthermore crossing between offspring heterozygous mice thereby and other C57BL-6 strain mice are repeated. It is preferable that the procedures of crossing be repeated at least 5 times. It is furthermore preferable to be repeated at least 7 times in total. In the present embodiments, the procedures of crossing between the heterozygous mice-F1 and C57BL-6J strain mice, and furthermore crossing between offspring heterozygous mice thereby and other C57BL-6 strain mice were repeated 6 times to prepare heterozygous mice-F7. Finally female heterozygous mice-F7 were crossed with male heterozygous mice-F7 to F8 of generate wild-type mice, heterozygous mice and homozygous mice (i.e. NF-κBp50-deficient mice). Each strain mice were used for evaluations of properties of eyes thereof such as property of retinal tissue, optic nerves tissue and intraocular pressure, with comparison themselves.

(Western Blot Analysis)

The retinas were dissected from mouse eyes (NF-κBp50-deficient mice-F8) and homogenized in modified RIPA buffer solution (50 mM Tris (pH7.4), 1% NP-40 (surface-active agent), 0.25% Na-deoxycholic acid, 150 mM NaCl, 1 mM EDTA (ethylenediaminetetraacetic acid), 1 mmol NaF, 1 mM PMSF (phenylmethylsulfonyl fluoride), 1 mM $Na_3Vo_4$, and 1 µg/mL each of aprotinin, leupeptin and pepstatin). The samples were first heated at 95° C. for 10 minutes and then centrifuged at 15000 rpm for 20 minutes and the supernatants were stored as retinal crude extracts at −30° C. These extracts (10 µg) were run on 10% SDS-PAGE (sodium dodecyl sulfate-polyacetylamide gel electrophoresis), and immunoblot analysis was performed with rabbit polyclonal antibodies to NF-κBp65 or p50 (Santa Cruz Biotechnology Inc., CA, USA) and goat polyclonal antibodies to glial fibrillary acidic protein (GFAP) (Santa Cruz Biotechnology Inc., CA, USA) under the standard procedure. Immuno-detectable proteins were visualized and enhanced using the ECL Western blot system (GE Healthcare Bio-Sciences Ltd., Sweden).

(Retinal Ganglion Cell (RGC) Labeling and Count)

The mice were anesthetized by intraperitoneal administration of a mixture of xylazine (10 mg/kg) and ketamine (70 mg/kg). The skin over the cranium was incised, and the scalp was exposed. The designated point of injection was at a depth of 2 mm from the brain surface, 3 mm behind the bregma in the anteroposterior axis and 0.5 mm lateral to the midline. A window was drilled in the scalp, and the neurotracer dye FluoroGold (4% solution in saline; Fluorochrome, LLC, Denver Colo., USA) was applied (1 µl at a rate of 0.5 µl/min. in each hemisphere) using a Hamilton syringe, and the skin over the wound was sutured. 5 to 7 days after the application of FluoroGold, the mice were euthanized and, after their eyes were enucleated, the retinas were detached as flattened whole mounts in 4% paraformaldehyde in PBS (phosphate buffer saline). Labeled cells from 10 fields of identical size (230×150 µm) were counted under a fluorescence microscope. The counted fields were located at approximately the same distance from the ora serrata (500 µm). The fields were counted by 2 blinded observers, and the average number of RGCs per field was calculated for each retina and was analyzed by ANOVA (analysis of variance) with Bonferroni correction.

(Nucleosome DNA Fragmentation Analysis)

Isolated retinas from the mice were placed into 500 ml of buffer solution A (10 mM Tris-HCl (pH7.8), 3 mM $MgCl_2$, 1 mM EDTA) containing NP-40 at the final concentration of 0.1%, and were homogenized. After centrifugation (cfg. 2300 rpm, 5 min.), the nuclei were isolated as a pellet, re-suspended in lysis solution (50 mM Tris-HCl (pH7.8), 10 mM EDTA, 0.5% sodium lauroylsarcosinate) containing ribonuclease (RNase) A solution (final concentration of 1 mg/ml) and Proteinase K (final concentration of 1 mg/mL), and incubated at 50° C. for 15 min. After incubation, the sample was stored as nucleosome DNA at −30° C. and then run on 10% agarose gel under the standard procedure to analyze nucleosome DNA fragmentation for the detection of apoptotic cells.

(Intraocular Pressure (IOP) Measurement)

Intraocular pressure was recorded for the wild-type, the heterozygous and the homozygous mice (littermates of NF-κBp50-deficient F8 mice). The mice were slightly anesthetized with an intraperitoneal injection of pentobarbital sodium (40 mg/kg). Intraocular pressure was then determined in sequence by trained observers, beginning 10 min. after the induction of anesthesia, using the TonoLab rebound tonometer (Colonial Medical Supply Co., Inc., Garland, Tex., USA). Statistical differences were analyzed by the Student's t test.

(Morphometry and Transmission Electron Microscopy)

After anesthesia, transcardial perfusion was performed with 4% paraformaldehyde, and the optic nerves were dissected starting at 2 mm behind the globe and placed in fixative (approximately 20 ml of 2.0% glutaralaldehyde and 2.0% paraformaldehyde in 0.1 M cacodylate buffer solution) for 12 hours. The optic nerves were then postfixed in 1% osmium tetroxide, dehydrated in ethanol and embedded in EPOK812 (Okenshoji Co., Ltd., Tokyo, Japan). For transmission electron microscopy, ultrathin sections were cut perpendicular to the long axis of the optic nerves on an ultramicrotome, stained with uranyl acetate and lead citrate, and examined on a JEM1200EX transmission electron microscope (JEOL, Ltd., Tokyo, Japan). For light microscopic observation, toluidine blue staining was used, (NMDA Injection and Morphometric Analysis)

Intravitreal NMDA injection was performed. 2 µl of 5 mM solution of NMDA in buffered saline solution (BSS) was injected into the vitreous of the left eye of each mouse aged 2 months. The right eyes were injected with BSS alone. At 24 hours and 4 days after injection, the eyes were enucleated and fixed in 4% paraformaldehyde in PB, followed by dehydration and paraffin embedding. Tranverse sections were made through the optic disc and stained with hematoxylin and eosin (H&E). Cells of 0.35 mm length at 0.3 mm from the edge of the optic disc in the ganglion cell layer were counted except for cells infiltrating the ganglion cell layer. The average number of cells per field was analyzed, and statistical differences were analyzed by the Student's t test.

(Immunohistochemical (IHC) Staining)

Paraffin-embedded retinas and optic nerves were used for IHC. The sections were dewaxed and incubated in 1% BSA (bovine serum albumin). The sections were then incubated with the appropriate antibodies overnight at 4° C. The used primary antibodies were the goat polyclonal antibody to GFAP, rabbit polyclonal antibodies to NF-κBp50 or p65 (1:200, Santa Cruz Biotechnology, Inc., CA, USA) and rabbit polyclonal antibodies to CD3, CD11b or Gr-1 (BD PharMingen, CA, USA). At the end of incubation, the sections were washed and incubated with the second antibody, Alexa Fluor 488-conjugated anti-goat or anti-rabbit IgG (1:200, Santa Cruz Biotechnology, CA, USA). Finally, the sections were coverslipped with antifade mounting medium (VECTASHILD, Vector Lab., CA, USA) and visualized using a confocal microscope (Carl Zeiss Inc., Thornwood, N.Y., USA). Normal goat or rabbit antiserum was used as a negative control.

(Identification of Autoantibody Production in NF-κBp50-Deficient Mice)

Serum samples were obtained from NF-κBp50-deficient mice and wild-type mice. Paraffin-embedded retina sections derived from the wild-type mice were stained with serum samples, and IHC was visualized under the standard methods. Autoantibody production that directly recognizes retinal proteins was identified. For Western blot analysis, retina extracts from the wild-type mice aged 2 months were run on 10% SDS-PAGE as described previously, and immunoblot analysis was performed with serum samples derived from the NF-κBp50-deficient mice and wild-type mice aged 5 months.

Hereunder, the results of these experiments are shown.

(NF-κB Expression in the Retina)

NF-κB is expressed in the nervous system and plays important roles in such processes as synaptic activity, learning and memory. Since there is no report that examined the function of NF-κBp50 in the retina, we first investigated NF-κB expression in the retina by immunohistochemistry and Western blot analysis with antibodies to NF-κB subunits. According to the immunohistochemistry, NF-κBp65 and p50 expressions were detected in the cytoplasm of cells in the retina ganglion cell layer (GCL). Although RGCs make up approximately 40-60% of the neurons in the ganglion cell layer (GCL) of the mouse retina and a half of the cells are amacrine cells in the retinas, NF-κBp65 and p50 expressions were detected in almost all neurons in the retina ganglion cell layer. IHC with normal rabbit IgG did not recognize anything, suggesting that NF-κBp65 and p50 are specifically expressed in the cytoplasm of cells of GCL. By Western blot analysis, NF-κBp65, p50 and its precursor protein p105 expression were defected in retinal crude extracts derived from both types of mice.

(Age-Dependent Decrease of RGCs Survival in Retina of NF-κBp50-Deficient Mice)

Histological examination showed the retinas of NF-κBp50-deficient mice at 3 weeks of age to be normal and indistinguishable from those of wild-type mice. At 5 months, there was no difference in the thickness and construction of each retinal layer, especially the inner nuclear layer and outer nuclear layer. In the central nervous system, NF-κB is expressed ubiquitously in both neuronal and glial cells where it plays a key role in various physiological mechanisms such as synaptic activity, survival and apoptosis. The number of RGCs in NF-κBp50-deficient mice of different age was investigated, and it was demonstrated whether NF-κBp50 expression is required for RGCs survival. The number of RGCs from the mice at age of 3 weeks, 2 months and 5 months was counted by retrograde labeling methods using FluoroGold. The results are shown in FIGS. 1a and 1b.

Figure 1:
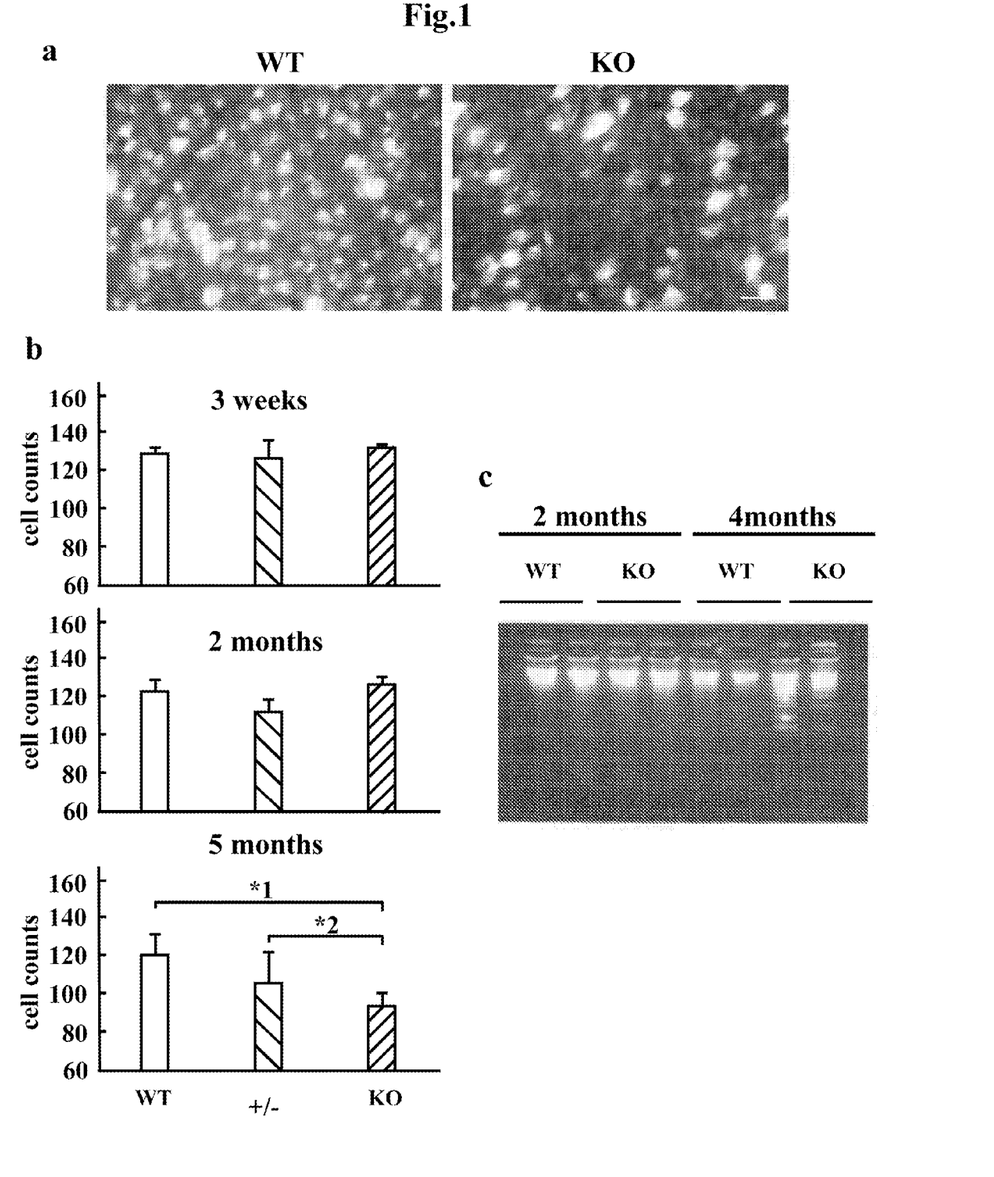
FIG. 1 is photographs and bar graphs representing age-related ganglion cell death in wild-type mice (WT mice) and NF-κBp50-deficient mice (KO mice: Knockout mice) of the normal-tension glaucoma model of the present invention.

Representative photographs of FIG. 1a shows that 5 to 7 days after the application of FluoroGold, the mice eyes were enucleated and flat mounted, and then the RGCs were counted by retrograde labeling method. Scale bar is 25 µm.

FIG. 1a represents bar graphs which show age-related decreasing ganglion cell number in NF-κBp50-deficient mice. Retrogradely labeled cells from 10 fields of identical size (230×150 µm) in the flat mounted retinas were counted under the fluorescence microscope. The counted fields were located at approximately the same distance from the ora serrata (500 µm). The average number of RGCs per field was calculated for each retina and was analyzed by analysis of variance (ANOVA) with Bonferroni correction. The bar graphs show the average number of RGCs per field at 3 weeks, 2 months and 5 months of age. Data are mean±SEM (n=3-week old: each 4, 2-month old: each 3-5, 5-month old: each 8-12). *1p<0.01 versus wild-type mice and *2p<0.01 versus wild-type mice.

As shown in FIG. 1a and 1b, at 5 months, the number of RGCs of p50-deficient-F8 mice had markedly decreased compared to age-matched littermate wild-type mice, and neuronal lesion of significant number of RGCs death was observed, although there was no significant difference between them at 3 weeks and 2 months. Additional histological experiments on the littermates of F3 mice generated by backcrossing with C57BL/6J mice were performed. The number of RGCs in mice at age of 3 weeks, 2 months and 5 months was counted using retrograde labeling methods. At 5 months old, the number of RGCs in p50-deficient-F3 mice was markedly decreased compared to age-matched littermate wild-type mice, although there was no significant difference between them at 3 weeks and 2 months.

Furthermore, to investigate whether decreasing RGCs survival is caused by apoptosis, nucleosome DNA fragmentation assay with retinal sections was performed. The results of nucleosome DNA fragmentation analysis for detection of apoptosis of ganglion cells are shown in FIG. 1c.

FIG. 1c shows the results of nucleosome DNA fragmentation analysis where retinas were excised from the mice of 2 weeks and 4 months of age and DNA fragmentation assay was performed.

FIG. 1c shows that the nucleosome DNA ladder was clearly detected in the retina of NF-κBp50-deficient mice at 4 months of age, but it was not detected in both types of mice at 2 months of age.

(No-Difference in IOP Between Wild-Type Mice and NF-κBp50-Deficient Mice)

In human glaucoma, it is known that RGCs death is often caused by high intraocular pressure. To demonstrate the possibility that RGCs death detected in NF-κ50-deficient mice is induced by high intraocular pressure as in human glaucoma, intraocular pressure was measured. The results are shown in FIG. 2.

Figure 2:
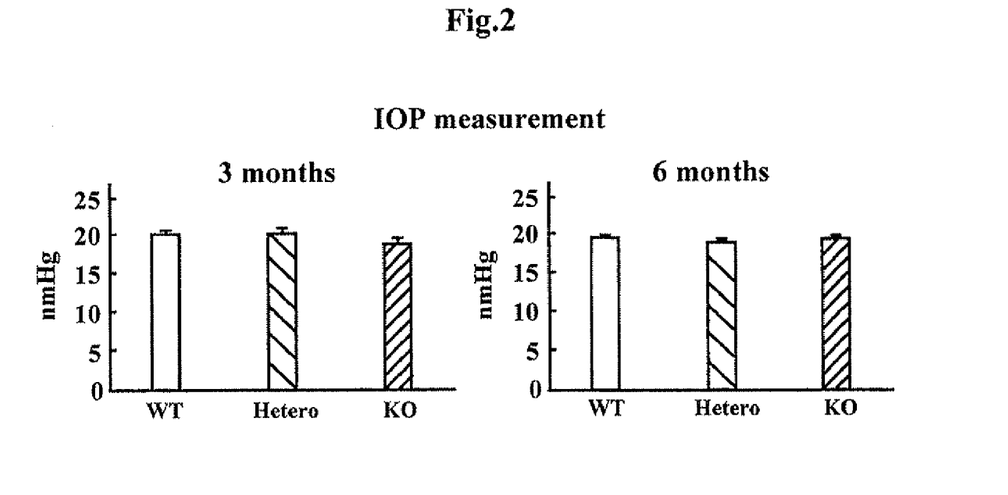
FIG. 2 is bar graphs representing intraocular pressure calculated for each eye obtained from wild-type mice, heterozygous mice (+/− mice: Hetero. mice) and NF-κBp50-deficient mice of the normal-tension glaucoma model of the present invention.

FIG. 2 shows that the intraocular pressure was calculated for each eye individually obtained from mice at 3 and 6 month of age. Data are mean±SEM (n=3-month old: each 5-6 mice, 6-month old: each 8-10 mice).

Intraocular pressure of normal wild-type mice is generally between 10 to 20 mmHg, but as shown in FIG. 2, in both 3-month-old mice and 6-month-old mice, there was no difference among wild-type mice, heterozygous mice and NF-κBp50-deficient mice, and intraocular pressure was within the normal range. Thus, high intraocular pressure does not correlate to RGCs loss in aged NF-κ50-deficient mice.

(Characteristic Excavation of Optic Nerve Head and Degenerative Changes of the Optic Nerve in NF-κBp50-Deficient Mice)

Since degenerative changes of the optic nerve are another hallmark of glaucomatous neuropathy, the age-related abnormality of optic nerves in NF-κBp50-deficient mice was examined. It is known that human glaucoma is defined by the characteristic excavation of optic nerve head. To assess the morphology of optic nerves in aged NF-κBp50-deficient mice, histological examinations were performed. In all wild-type mice, heterozygous mice and NF-κBp50-deficient mice aged 5 months or under, no constriction or excavation of the optic nerve head was observed. However, the histological results showed obvious excavation of the optic nerve head in mice at 10 months of age. The results at the age of 10 months are shown in FIG. 3a.

FIG. 3a shows the characteristic excavation of the optic nerve head and the degenerative changes of the optic nerve in NF-κBp50-deficient mice. FIG. 3a are photographs representing the histological results where the eyes were excised from 10-month-old mice and the sample sections were stained with Hematoxilin-Eosin (H&E).

As shown in FIG. 3a, in both wild-type mice and heterozygous mice, there was no histological abnormality of the optic nerve head, but the impressive abnormality of clear excavation of the optic nerve head in NF-κBp50-deficient mice was observed.

Figure 3:
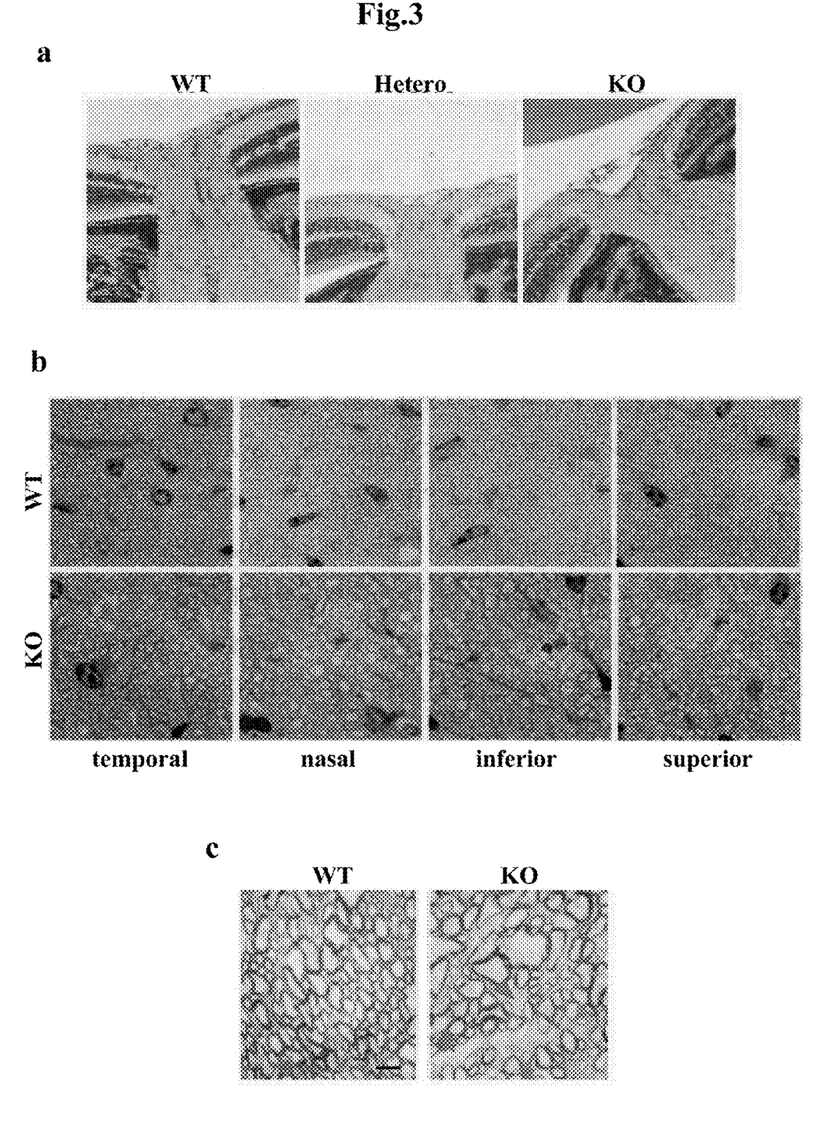
FIG. 3 is photographs representing excavation of an optic nerve head and degenerative changes of an optic nerve (atrophia and enlargement of the optic nerve), which are characteristic clinical findings of normal-tension glaucoma, in wild-type mice, heterozygous mice and NF-κBp50-deficient mice of the normal-tension glaucoma model of the present invention.

It has been confirmed that no histological abnormality such as excavation of the optic nerve heard is observed in the retina of normal person while it has been confirmed that excavation of the optic nerve heard is observed as characteristic pathological findings in the retina of normal-tension glaucoma patients. The excavation of the optic nerve head in NF-κBp50-deficient mice represented in FIG. 3 is similar to pathological findings of the excavation of the optic nerve head that is a specific characteristic of normal-tension glaucoma patients.

Then, to assess whether the optic nerves of aged NF-κBp50-deficient mice showed regional loss, histological examination was performed. Light microscopy showed no difference in thickness between the wild-type mice and NF-κBp50-deficient mice in cross sections of the optic nerve. However, in aged NF-κBp50-deficient mice, serious axonal alterations in all quadrants (temporal, nasal, inferior, superior) of optic nerves as well as atrophia and enlargement of the RGCs connecting to the brain via the optical nerve head were observed, and regional abnormal change by accident was not observed (FIG. 3b). Therefore, it seems that atrophia and enlargement of the RGCs is not to depend on a physical factor due to elevated intraocular pressure.

Furthermore, FIG. 3c shows electron microscopic examination for detection of alterations in each optic nerve axon (Magnification: X 8000), and the expanded-areas of each axon in NF-κ50-deficient mice at 5 months of age are indicated. Scale=2 μm. As shown in FIG. 3c, the number of each axon in NF-κBp50-deficient mice at 5 months of age decreased considerably compared to the wild-type mice. Under an electric microscope analysis of cross-sectioned optic nerves, it was confirmed that the area of each axon in NF-κBp50-deficient mice at 5 months of age expanded rather more than age-matched wild-type mice, in association with a decreasing number of axons. Therefore, the area of connective tissue surrounding the axons was significantly increased in NF-κBp50-deficient mice.

These findings are very interesting because they are very different from any other rodent model of glaucoma as already reported. Furthermore, NF-κBp50-deficient mice at 10 months of age, which exhibited clear excavation of optic disc, showed markedly impaired nerve fiber layer in the retina; however, significant death of INL cells was not observed as well as age-matched wild-type littermates. Therefore, it seems that atrophia and enlargement of the RGCs is not to depend on a physical factor due to elevated intraocular pressure.

(Increasing Glial Fibrillary Acidic Protein (GFAP) Expression in the Retina and Optic Nerve in NF-κBp50-Deficient Mice)

Glial cells are important structural and functional components of the nervous system including the optic nerve head and retina. There are several types of glial cells in human and mouse ocular tissues. In the optic nerve, glial cells include astrocytes, oligodendrocytes and microglia. In the retina, there are mainly Müller cells and astrocytes. If central neuronal cells are injured from any cause and become dead cells by apoptosis or necrosis, glial cell (astrocyte cell) becomes activated to act as phagocytes which indicates positive GFAP. The morphological change of the glial cell has been drawing attention in human glaucomatous eyes and glaucoma animal models.

The results of microscopic examination of cross-sectioned optic nerves are shown in FIG. 4a. FIG. 4a shows the microscopic examination performed on sample sections of the optic nerves respectively excised from mice at 2 and 5 months of age were stained with toluidine blue. The arrows indicate hypertrophic astrocytes, Scale bar is 10 μm. As shown in FIG. 4a, the morphology of astrocytes in NF-κBp50-deficient mice at 5 months of age apparently changed to hypertrophy compared to age-matched wild-type mice, while there was no difference between both types of mice at 2 months of age.

Figure 4:
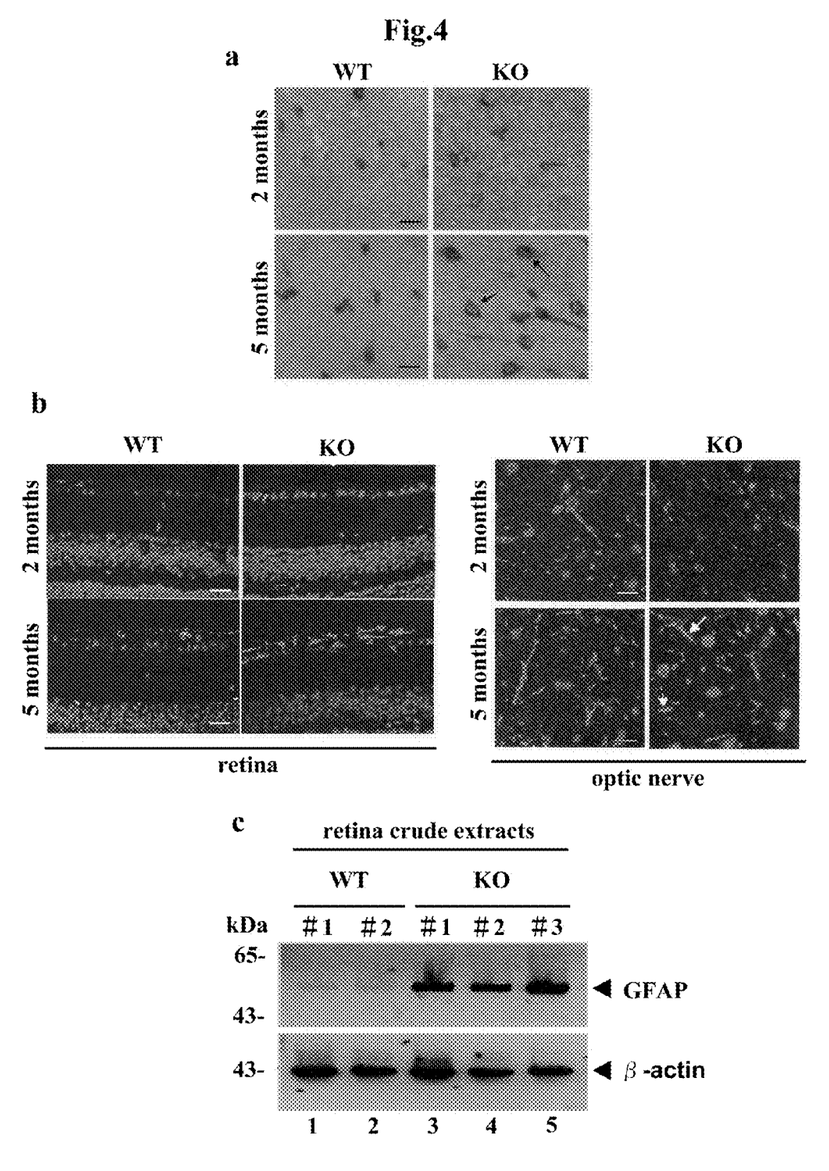
FIG. 4 is photographs representing glial cell activation in a retina and an optic nerve of wild-type mice and NF-κBp50-deficient mice of the normal-tension glaucoma model of the present invention.

Then, immunohistochemistry (IHC) was performed, and the results thereof are shown in FIG. 4. The glial cell activation is determined by being positive GFAP. FIG. 4b shows the glial cell activation in the retina and the optic nerve of NF-κBp50-deficient mice shown by IHC with anti-GFAP antibody. The retinal cross sections are shown in the left 4 photographs, and the scale bar is 10 µm. The optic nerve cross sections are shown in the left 4 photographs, and the scale bar is 20 µm.

In retina, there are two distinct types of macroglial cells namely astrocytes and Müller cells. In those 4 photographs on the left side of FIG. 4b showing the retinal cross sections, upper region (retinal ganglion cell layer) of the bright section shows astrocytes, and middle region of the dark section shows Müller cells While the activated Müller cells are not positive GFAP, the activation of astrocytes can be determined as it is positive GFAP. As shown in 4 photographs on the left side of FIG. 4b, all sample sections of wild-type mice aged 2 months and 5 months, and NF-κBp50-deficient mice aged 2 months demonstrated no GFAP immunoreactivity, in short activation of astrocytes was not detected. However, the sample sections of NF-κBp50-deficient mice aged 5 months were positive GFAP, in short activation of glial cells was observed.

As shown in 4 photographs on the right side of FIG. 4b, the sample sections of the optic nerves excised from wild-type mice aged 2 months and 5 months, and NF-κBp50-deficient mice aged 2 months were not positive GFAP, in short activation of astrocytes was not detected. On the other hand, as indicated by arrows, the sample sections of NF-κBp50-deficient mice aged 5 months were positive GFAP, in short activation of astrocytes was observed.

As represented in FIG. 4b, GFAP was markedly expressed in the nerve fiber layers and ganglion cells in NF-κBp50-deficient mice aged 5 months compared with those of wild-type mice. IHC analysis with both wild-type mice and NF-κBp50-deficient mice at 5 months of age demonstrated no GFAP immunoreactivity coursing through the inner nuclear layer. In other words, activation of Müller cells was not detected in either wild-type mice or NF-κBp50-deficient mice at 5 months of age. In 2-month-old mice, only a few astrocytes were faintly stained with GFAP in the retinas of both wild-type mice and NF-κBp50-deficient mice. In addition to increasing GFAP expression, which means activation of astrocytes, in the retinas of older NF-κBp50-deficient mice, optic nerve cross-sections clearly showed both hypertrophy of astrocyte cell bodies and a thicker network of processes in the optic nerve in NF-κBp50-deficient mice.

It is known that while only a few astorcytes are faintly stained with GFAP in the normal optic nerve cross-sections, GFAP-positive activated astrocytes are detected in the retinal ganglion cell layer of the retinal tissue cross-sections in normal-tension glaucoma patients. Also, the same applies to the sections of the optic nerves. The nerve fiber layer and the ganglion cells excised from NF-κBp50-deficient mice aged 5 months exhibited features resembling histology of human glaucoma.

FIG. 4c shows GFAP expression in the retinas of NF-κBp50-deficient mice demonstrated by Western blot analysis. Each retina was respectively obtained from 2 wild-type mice and 3 NF-κBp50-deficient mice, and Western blot analysis was performed with retinal crude protein extracts and appropriate antibodies. As FIG. 4c shows, GFAP expression of a glial cell activation marker was markedly detected in retinal crude protein extracts derived from NF-κBp50-deficient mice at the age of 6 months, while no band was detected in that from wild-type mice. As represented in FIG. 4c, Western blot results strongly support the immunohistochemistry (IHC) experiments. In a recent report, human normal paraffin-embedded retina stained IHC with GFAP demonstrated that only a few astrocytes were faintly stained with GFAP. In contrast, human glaucomatous paraffin-embedded retina stained IHC with GFAP demonstrated that GFAP-positive astrocytes in the glaucomatous retina increased significantly. Furthermore, these IHC results show that no GFAP immunoreactivity coursing through the inner nuclear layer. In short, Müller cells are not positive GFAP (i.e. activated) in human glaucomatous retinal tissue and NF-κBp50-deficient mice retinal tissue. Thus, existence of localized GFAP-positive cells (i.e. activated astrocytes) in retina of NF-κBp50-deficient mice was quite similar to existence of localized GFAP-positive cells of the retinal tissue of human glaucoma.

(Susceptibility of NMDA-Induced Neurotoxicity in NF-κBp50-Deficient Mice)

Since NMDA receptor-mediated excitotoxicity has been reported to contribute to glaucomatous neuropathy and the NMDA receptor-mediated potassium efflux leads apoptosis of the neurons, the effect of NF-κBp50 on NMDA-induced neurotoxicity was examined. NMDA has excitotoxicity at a high concentration of 100 nmol which promptly leads cell death. The results of histological examination of the retinas at 24 hours after intravitreal injection of 10 nmol NMDA, which is a relatively low concentration as for NMDA-induced neurotoxicity, are shown in FIG. 5.

Figure 5:
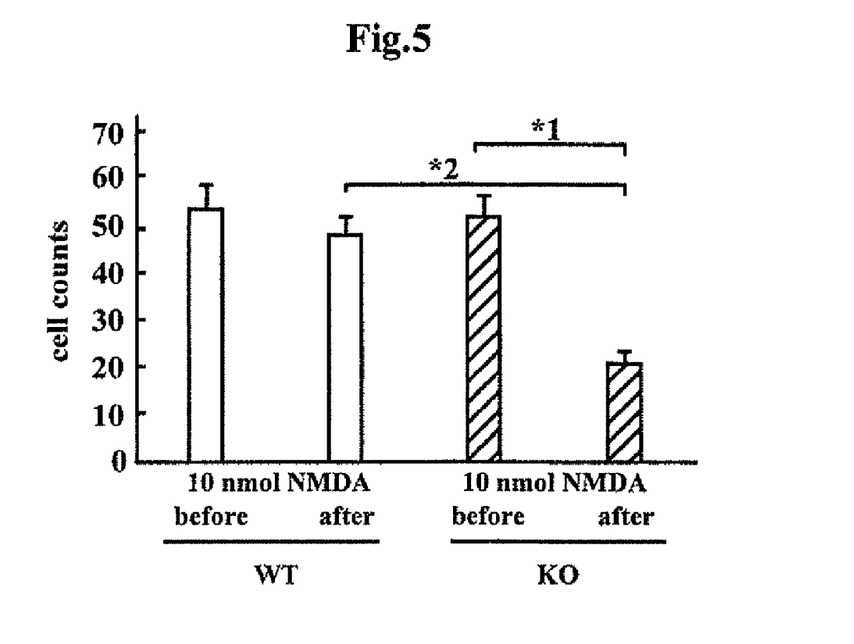
FIG. 5 is a bar graph representing the sensitivity of retinal ganglion cells (RGCs) of wild-type mice and NF-κBp50-deficient mice of the normal-tension glaucoma model of the present invention against NMDA toxicity.

FIG. 5 shows a decreasing live cell number in retinal ganglion cell layer (GLC) of NF-κBp50-deficient mice (2 months old) after NMDA treatment. The live cells were counted in length of 0.35 mm at 0.3 mm each from the edge of the optic disc. Bar graphs show the number of cells in GCL at time before and 24 hours after NMDA-treatment. The average number of cells per field was analyzed by the two-tailed t-test. Statistical differences were analyzed by the Student's t test. Data are mean±SEM (n=6 to 7 mice). *1p<0.01 versus wild-type mice. *2p<0.01 versus wild-type mice.

As shown in FIG. 5, a more decreasing number of retinal ganglion cells was observed in NF-κBp50-deficient mice than in wild-type mice; however, no significant difference in inner plexiform layer thickness was observed between NF-κBp50-deficient mice and wild-type mice. Also, at 24 hours after NMDA treatment, a relatively increased number of infiltrating cells was observed in NF-κBp50-deficient mice than in wild-type mice in the ganglion cell layer and vitreous cavity. However, at 4 days after NMDA treatment, no infiltrating cells were detected in both the retina and optic nerves. IHC analysis showed that most infiltrating cells in the retina were CD11b-positive macrophages and Gr-1-positive neutrophils. In NF-κBp50-deficient mice, 10 nmol NMDA treatment for 24 hours markedly induced cell death in GCL, but no significance was observed in wild-type mice.

It seems that as the retinal ganglion cell death of NF-κBp50-deficient mice is caused by apoptosis due to chronic physiological mechanism. It seems that the glial cells in the retina (i.e. astrocytes) were activated to be phagocytes that ingest retinal ganglion cells dead by apoptosis. Macrophages and neutrophils perhaps acutely invaded inner plexiform layer and ganglion cell layer to phagocyte NMDA treatment-induced dead cells. To verify NF-κBp50 activation by NMDA treatment in NF-κBp50-deficient mice and wild-type mice, IHC analysis with NF-κBp65 antibody was performed. HC showed that NF-κBp65 noticeably translocated to the nucleus in GCL, was well as NF-κBp50 in wild-type mice. The effect of NMDA on NF-κB activation in RGCs of NF-κBp50-deficient mice was clearly detected.

Then, the relationship between the expression or activation of NF-κBp65 and the symptoms of normal-tension glaucoma was investigated as follows.

(Susceptibility of NMDA-Induced Neurotoxicity at Different Concentration in Wild-Type Mice and NF-κBp50-Deficient Mice)

Figure 6:
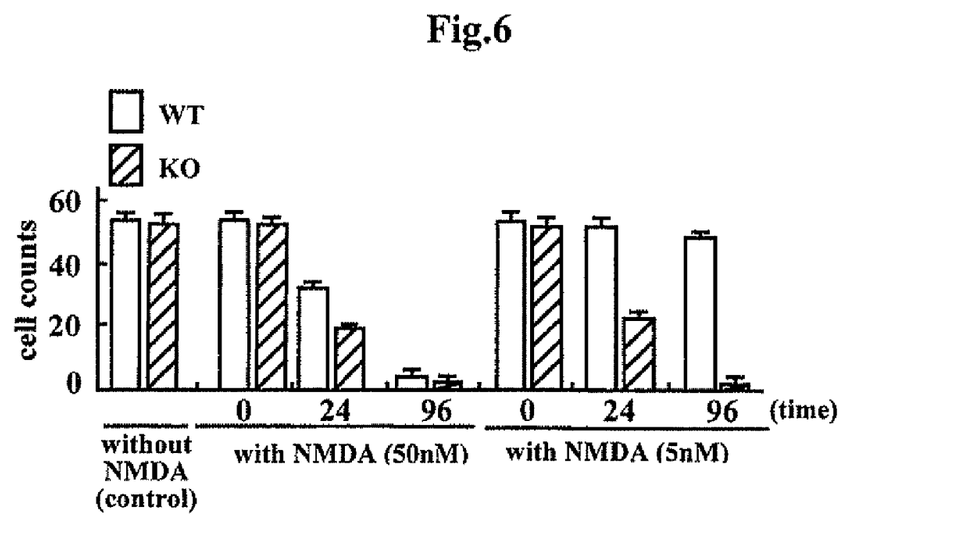
FIG. 6 is a bar graph representing the sensitivity of retinal ganglion cells (RGCs) of wild-type mice and NF-κBp50-deficient mice of the normal-tension glaucoma model of the present invention against NMDA toxicity.

50 nM and 5 nM of NMDA were directly administered into vitreous respectively, and then the number of live ganglion cells was counted. As a control, the number of live ganglion cells without administration of NMDA was also counted. The results are shown in FIG. 6. As shown in FIG. 6, in the case of wild-type mice and NF-κBp50-deficient mice with injection of 50 mM NMDA, which is a relatively high concentration, about half the ganglion cells thereof were dead by apoptosis within 24 hours after NMDA treatment, and moreover almost all of the ganglion cells were dead by apoptosis within 96 hours (4 days). On the other hand, in the case of wild-type mice and NF-κBp50-deficient mice with injection of 5 nM NMDA, which is a relatively low concentration, while almost all of the ganglion cells in wild-type mice survived at 4 days after NMDA treatment, about 60% of the ganglion cells in NF-κBp50-deficient mice were dead within 24 hours by apoptosis and moreover almost all of them were dead within 96 hours. This revealed that decrease in NF-κBp50 activation in the ganglion cells markedly increase the susceptibility of NMDA-induced apoptosis.

Hereunder, examples of evaluation of therapeutic effect of test substances on normal-tension glaucoma as well as screening of a drug useful as normal-tension glaucoma therapeutic agent are explained.

(Screening of Test Substances)
(Preparation of Control Group with Administration for 7 Days)

Figure 7:
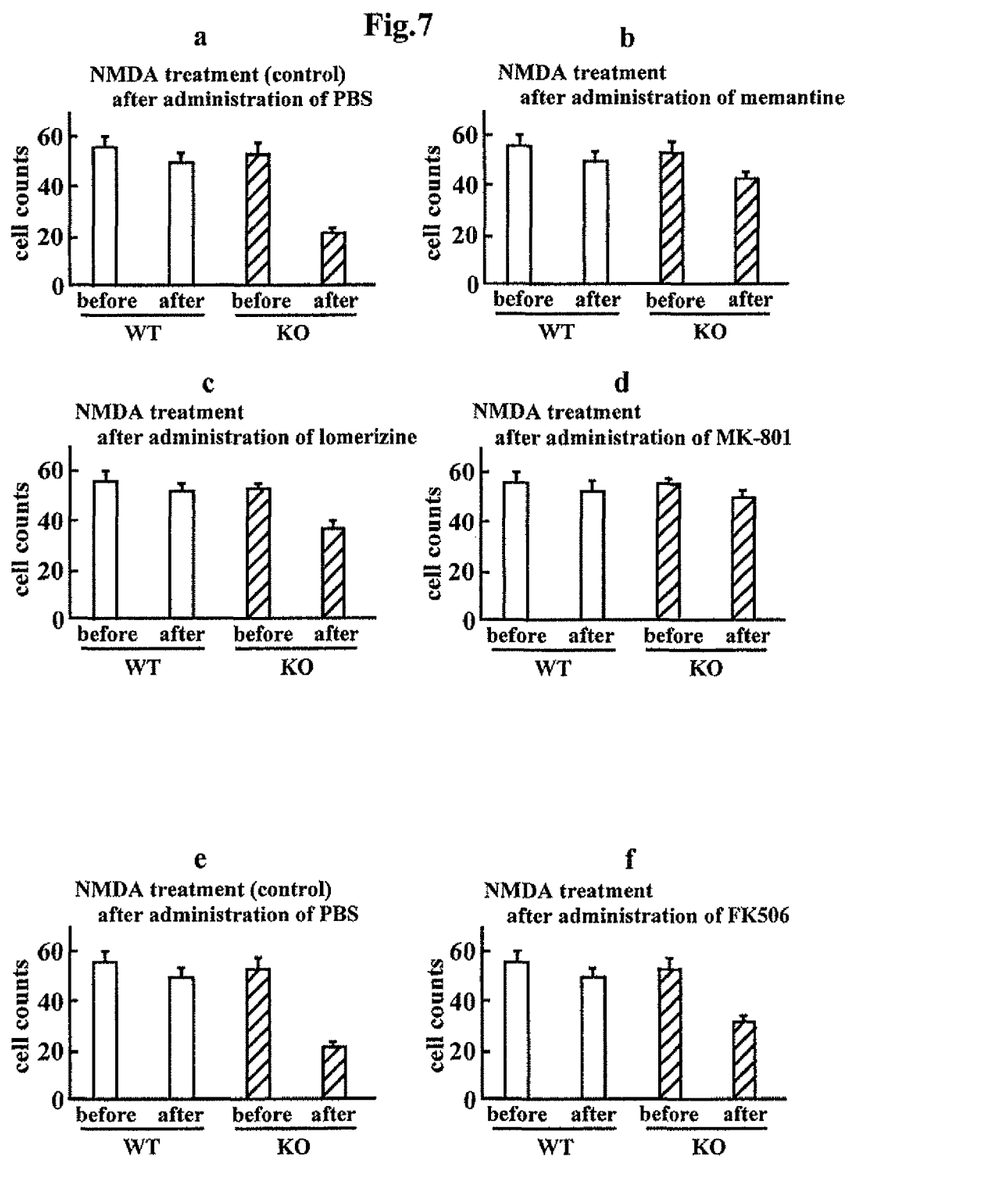
FIG. 7 shows bar graphs representing therapeutic effects of the test substances on wild-type mice and NF-κBp50-deficient mice of the normal-tension glaucoma model by method for evaluation of therapeutic effect on normal-tension glaucoma of the present invention.

By intraperitoneal administration, phosphate buffered saline (PBS) as control substance was respectively administered to wild-type mice and NF-κBp50-deficient mice once daily for 7 days. 5 mM of NMDA was directly administered into vitreous of the mice, and then the number of retinal ganglion cells after 24 hours was counted. The results are shown in FIG. 7a. As shown in FIG. 7a, while only about 6% of retinal ganglion cells in wild-type mice were dead by apoptosis within 24 hours after administration of NMDA, about 60% of retinal ganglion cells in NF-κBp50-deficient mice were noticeably dead by apoptosis within 24 hours after administration of NMDA.

(Screening of a Test Substance: Memantine)

By intraperitoneal administration, 10 mg/kg of memantine hydrochloride, which is used as a curative medicine for Alzheimer type dementia and is an antagonist of NMDA receptor as one of glutamic acid receptor, was respectively administered to wild-type mice and NF-κ50-deficient mice once daily for 7 days. 5 mM of NMDA was directly administered into vitreous of the mice, and then the number of retinal ganglion cells after 24 hours were counted. The results are shown in FIG. 7b. As shown in FIG. 7b, only about 3% of retinal ganglion cells in the wild-type mice were dead by apoptosis within 24 hours after administration of NMDA, and also only about 15% of retinal ganglion cells in NF-κBp50-deficient mice were dead by apoptosis within 24 hours after administration of NMDA.

(Screening of a Test Substance: Lomerizine)

100 mg/kg of lomerizine hydrochloride, which is used as a curative medicine for migraine and is a piperazine-type calcium inhibitor, was respectively administered orally via catheters to wild-type mice and NF-κBp50-deficient mice once daily for 7 days. 5 mM of NMDA was directly administered into vitreous thereof, and then the number of retinal ganglion cells after 24 hours was numerated. The results are shown in FIG. 7c. As shown in FIG. 7c, only about 2% of retinal ganglion cells in the wild-type mice only were dead by apoptosis within 24 hours after administration of NMDA, and also no more than about 28% of retinal ganglion cells in NF-κBp50-deficient mice only were dead by apoptosis within 24 hours after administration of NMDA.

(Screening of a Test Substance: MK-801)

By intraperitoneal administration, 10 mg/kg of MK-801, which is NMDA receptor antagonist and is (5S,10R)-(−)-5-methyl-10,11-dihydro-5H-dibenzo[a,d]-cyclo-hepten-5,10-imine hydrogen maleate, was respectively administered to wild-type mice and NF-κBp50-deficient mice once daily for 7 days. 5 mM of NMDA was directly administered into vitreous thereof, and then the number of retinal ganglion cells after 24 hours was counted. The results are shown in FIG. 7d. As shown in FIG. 7d, only about 2% of retinal ganglion cells in the wild-type mice only were dead by apoptosis within 24 hours after administration of NMDA, and also no more than about 9% of retinal ganglion cells in NF-κBp50-deficient mice only were dead by apoptosis within 24 hours after administration of NMDA.

As the above results indicate, it is obvious that those test substances, especially memantine hydrochloride and MK-801 had pharmacological effects of protecting retinal ganglion cells from NMDA-induced apoptosis.

And it has been known that neurons are led to apoptosis according to NMDA-receptor-mediated calcium efflux. NMDA-induced apoptosis activates phosphatase calcineurin by potassium efflux into the neurons. Specifically, it is supposed that transient activation of potassium induces the neurons to apoptosis. And it is supposed that activation of calcineurin in the neurons under a state of ischemia caused by cerebral infraction is promoted remarkably to lead the apoptosis of the neurons. It develops that KF506 (i.e. prograf) of a calcineurin inhibitor acts as an immunosuppressant which inhibits cytokine production and protects neurons from injuries caused by cerebral infraction. Thereupon effects of KF506 for protecting of retinal ganglion cells from NMDA-induced apoptosis were investigated.

(Screening of a Test Substance: FK506)

A control group was kept alike with administration for 2 weeks instead of administration of PBS for 7 days under above-mentioned control group. The results of the control group with administration for 2 weeks are indicated in FIG. 7e. On the other hand, 3 mg/kg of KF506 was respectively administered to wild-type mice and NF-κBp50-deficient mice once daily for 2 weeks by intraperitoneal administration. 5 mM of NMDA was directly administered into vitreous thereof, and then the number of retinal ganglion cells after 24 hours was counted. The results are shown in FIG. 7f. As shown in FIG. 7f, only about 5% of retinal ganglion cells in the wild-type mice only were dead by apoptosis within 24 hours after administration of NMDA, and also no more than about 34% of retinal ganglion cells in NF-κBp50-deficient mice only were dead by apoptosis within 24 hours after administration of NMDA.

As shown in above results, it is obvious that FK506 had effect of protecting of the retinal ganglion cells from the NMDA-induced apoptosis.

(Production of Autoantibodies Against RGCs in NF-κBp50-Deficient Mice)

Several studies demonstrated that autoantibodies against RGCs participate in developing neuropathy in glaucoma patients. Furthermore, recent reports show potential autoantibody production in NF-κBp50-deficient mice. To investigate whether autoantibodies against RGCs are produced in NF-κBp50-deficient mice, IHC with serum derived from NF-κBp50-deficient mice or wild-type mice was carried out. The ganglion cell layer was clearly stained with serum derived from NF-κBp50-deficient mice, while no staining was observed with serum from wild-type mice. Furthermore, to confirm a possible autoimmunity function in aged NF-κBp50-deficient mice, Western blot analysis with antiserum derived from wild-type mice and NF-κBp50-deficient mice was carried out. The analysis results revealed that several autoantibodies, which directly recognized proteins in normal retinal crude extracts, were produced in NF-κBp50-deficient mice of 5 months of age; however, no band was detected from wild-type mice. The results of Western blot analysis support IHC experimental results with antiserum. Clearly showing that autoantibodies are produced in aged NF-κBp50-deficient mice and suggesting that this autoimmune mechanism might be involved in RGC death.

As described above, NF-κBp50-deficient mice showed many features resembling clinical findings of human normal-tension glaucoma such as development of RGCs cell death which frequently occurs in middle-aged and elder people, characteristic excavation of the optic nerve head, activation of astrocytes in retinas, atrophia and enlargement of the optic nerve, autoantibody production, and constant intraocular pressure age-independently. Therefore, it was confirmed that the NF-κBp50-deficient mouse was a animal model which spontaneously develop normal-tension glaucoma.

Then, another method for evaluation of therapeutic effect on normal-tension glaucoma, which screens a drug useful for human normal-tension glaucoma, using the normal-tension glaucoma model comprising NF-κBp50-deficient mice is investigated.

Clinically, it is found that most of normal-tension glaucoma patients have been troubled by migraine with aura, and so it is suggested that both of normal-tension glaucoma and migraine with aura may have common risk factors. Therefore, a calcium inhibitor used for medication for migraine with aura may be effective in medication for normal-tension glaucoma. It is known according to analysis of risk factors for migraine with aura that sensitive locus on chromosome thereof was forth chromosome 24 (4q24). Surprisingly chromosome of NF-κBp50 (MIN:164011) is coded on forth chromosome 24 (4q24). Specifically it is suggested that non-activation of NF-κBp50 may be one of the risk factors for normal-tension glaucoma. Activation of NF-κB is concerned in $Ca^{2+}$ signal cascade induced by stimulation of NMDA and so on. Therefore, a calcium inhibitor inhibits the activation of NF-κB. Consequently, the calcium inhibitors such as dihydropyridine derivatives and benzodiazepine derivatives may be curative medicines for normal-tension glaucoma. According to the method for evaluation of therapeutic effect of the present invention, expression of p50 using human glaucoma tissue allows to be investigated, and actually has been investigated.

As described in detail above, apoptosis of the ganglion cell was observed in NF-κBp50-deficient mice aged 4 months or older, and at the age of 5 months or older, significant decrease in the number of ganglion cells was observed. In NF-κBp50-deficient mice aged 7 months, unlike the mice aged 5 months, atrophy of ganglion cell layer was observed. Then, in NF-κBp50-deficient mice aged 10 months, characteristic excavation of the optic nerve head was observed. This confirmed that the retinal ganglion cell death by apoptosis in NF-κBp50-deficient mice was first observed, and then atrophy of optical nerve fiber layer or excavation of optic nerve head was gradually developed.

The prevalence according to age of human normal-tension glaucoma is 0.93% in age between 30 and 49, 1.86% between 50 to 69 and 4.89% in 70 and over, and development of normal-tension glaucoma can be gradually observed in middle-aged and elder people. The prevalences according to age of human normal-tension glaucoma is extremely similar to morbidities NF-κBp50-deficient mice of according to age in month.

Industrial Applicability

The normal-tension glaucoma model of the present invention comprises the nonhuman mammal that is deficient in the transcription factor NF-κBp50 which relates to human normal-tension glaucoma or the cells thereof, so the method for evaluation therapeutic effect on normal-tension glaucoma using the model can be used for investigation of pathogenic mechanism of normal-tension glaucoma in human of one of mammal, determination of the risk factor, screening of therapeutic agent or preventive drug and development of treating method or preventive method.

The therapeutic agent for normal-tension glaucoma of the present invention is useful in treating normal-tension glaucoma of unknown etiology. Furthermore, the method for diagnosing or risk-prediction of normal-tension glaucoma of the present invention is useful for early detecting and early treating of normal-tension glaucoma. And the therapeutic agent of the present invention is useful for curing normal-tension glaucoma.

What is claimed is:

1. A method for evaluating a therapeutic effect of a test substance on normal-tension glaucoma, comprising:
   (a) administering a test substance to a mouse having in its genome a homozygous disruption of transcription factor NF-κBp50 gene, wherein the mouse has the following symptoms that correspond to symptoms of human normal-tension glaucoma and are developed in the mouse due to the disruption of transcription factor NF-κBp50 expression: (i) normal intraocular pressure; (ii) constriction and excavation of optic nerve head periphery; (iii) loss of a retinal nerve fiber layer; (iv) metamorphosis and backward deviation of the optic nerve at the lamina cribrosa; and (v) a decrease in retinal ganglion cells and glial cells; and
   (b) measuring at least one of said symptoms (ii)-(v) in said mouse administered said test substance;
   wherein an improvement of said at least one of said symptoms (ii)-(v) measured in step (b) indicates that the test substance has a therapeutic effect on normal tension glaucoma.

2. The method for evaluation according to claim 1, further comprising:
   measuring said at least one of said symptoms (ii)-(v) in a second mouse having in its genome a homozygous disruption of transcription factor NF-κBp50 gene, wherein the mouse has the following symptoms that correspond to symptoms of human normal-tension glaucoma and are developed in the mouse due to the disruption of transcription factor NF-κBp50 expression: (i) normal intraocular pressure; (ii) constriction and excavation of optic nerve head periphery; (iii) loss of a retinal nerve fiber layer; (iv) metamorphosis and backward deviation of the optic nerve at the lamina cribrosa; and (v) a decrease in retinal ganglion cells and glial cells, wherein said second mouse does not receive the test substance; and comparing said at least one of said symptoms (ii)-(v) in said mouse administered the test substance to said at least one of said symptoms (ii)-(v) in said second mouse; wherein an improvement in said at least one said symptoms (ii)-(v) in said mouse administered said test substance as compared to said at least one said symptoms (ii)-(v) in said second mouse that does not receive the test substance indicates that the test substance has a therapeutic effect on normal tension glaucoma.

3. The method for evaluation according to claim 2, further comprising administering N-methyl D aspartate (NMDA) or a salt thereof in addition to the test substance.

4. The method for evaluation according to claim 1, wherein the test substance is at least one member selected from the group consisting of a NMDA receptor antagonist, a calcium inhibitor, an I-κB degradation inhibitor, a NF-κB decoy oligo nucleic acid and a calcineurin inhibitor.

* * * * *